United States Patent [19]

Gericke et al.

[11] Patent Number: 5,849,796
[45] Date of Patent: Dec. 15, 1998

[54] ORTHO-SUBSTITUTED BENZOIL ACID DERIVATIVES

[75] Inventors: Rolf Gericke, Seeheim-Jugenheim; Dieter Dorsch, Ober-Ramstadt; Manfred Baumgarth, Ober-Ramstadt; Klaus-Otto Minck, Ober-Ramstadt; Norbert Beier, Reinheim, all of Germany

[73] Assignee: Merck Patent Gelsellschaft mit Beschrankter Haftung, Germany

[21] Appl. No.: 520,340

[22] Filed: Aug. 28, 1995

[30] Foreign Application Priority Data

Aug. 28, 1994 [DE] Germany ............... 44 30 212.6

[51] Int. Cl.⁶ .................................. A61K 31/165
[52] U.S. Cl. ................ 514/618; 514/522; 514/599; 514/616; 514/821; 514/824; 514/866; 514/921; 558/412; 558/413; 567/74; 567/154; 567/162
[58] Field of Search .................. 564/162, 74, 154; 514/618, 821, 522, 599, 616, 824, 866, 921; 558/412, 413

[56] References Cited

U.S. PATENT DOCUMENTS 5,373,024  12/1994  Lang et al. .................... 514/618

FOREIGN PATENT DOCUMENTS 2024700  3/1991  Canada .
2089439  8/1993  Canada .
2089440  8/1993  Canada .
2106613  3/1994  Canada .
 416499  3/1991  European Pat. Off. .
 556673  8/1993  European Pat. Off. .
 589336  3/1994  European Pat. Off. .
 690 048  6/1995  European Pat. Off. .

OTHER PUBLICATIONS

Database Registry, Chemical Abstracts Service, Columbus OH, US.
Abstract of EP 690,048.

*Primary Examiner*—Peter O'Sullivan
*Attorney, Agent, or Firm*—Millen, White, Zelano, & Branigan, P.C.

[57] ABSTRACT

Ortho-substituted benzoic acid derivatives of the formula I

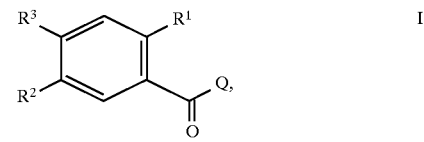

in which $R^1$, $R^2$ and $R^3$ have the given meanings, and Q is guanidyl, and also their physiologically harmless salts, exhibit antiarrhythmic properties and act as inhibitors of the cellular $Na^+/H^+$ antiporter. In addition, the compounds of the formula I, in which $R^1$ to $R^3$ and also Q have the given meanings, are suitable for use as valuable intermediates for the preparation of medicaments, in particular of inhibitors of the cellular $Na^+/H^+$ antiporter.

15 Claims, No Drawings

ORTHO-SUBSTITUTED BENZOIL ACID DERIVATIVES

The invention relates to ortho-substituted benzoic acid derivatives of the formula I

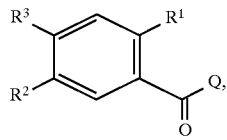

in which $R^1$ is A, $CF_3$, $CH_2F$, $CHF_2$, $C_2F_5$, CN, $NO_2$, Hal, C≡CH or —X—$R^4$, $R^2$ is $CF_3$, —$SO_n$—$R^6$ or —$SO_2NR^4R^5$, $R^3$ is CN, Hal, COA, CHO, $CSNR^7R^8$, or $CONR^7R^8$; or A, if Q is not —N=C($NH_2$)$_2$;

Q is —N=C($NH_2$)$_2$, Cl, Br, OA, O—CO—A, O—CO—Ph, OH, or another reactive esterified OH group or a leaving group which can readily be substituted nucleophilically, $R^4$ is H, A, cycloalkyl having from 5 to 7 C atoms, cycloalkylmethyl having from 6 to 8 C atoms, $CF_3$, $CH_2F$, $CHF_2$, $CH_2CF_3$, Ph or —$CH_2$—Ph, $R^5$ is H or A, or else $R^4$ and $R^5$ are together also alkylene having from 4 to 5 C atoms, where one $CH_2$ group can also be replaced by O, S, CO, NH, N—A or N—$CH_2$—Ph, $R^6$ is A or Ph, $R^7$ and $R^8$ are in each case, independently of one another, H, A or Ac, A is alkyl having from 1 to 6 C atoms, X is O, S or $NR^5$, Hal is F, Cl, Br or I, Ph is phenyl which is unsubstituted or is substituted once, twice or three times by A, OA, $NR^4R^5$, F, Cl, Br, I or $CF_3$, Ac is alkanoyl having from 1 to 10 C atoms, or aroyl having from 7 to 11 C atoms, and n is 1 or 2, and the pharmaceutically tolerated salts thereof.

An object of the invention is to discover novel compounds having valuable properties, in particular those compounds which can be used for preparing medicaments or as intermediates for preparing other active compounds.

Upon further study of the specification and appended claims, further objects and advantages of this invention will become apparent to those skilled in the art.

It was found that the compounds of the formula I, in particular those in which Q is —N=C($NH_2$)$_2$, and their physiologically tolerated salts, possess valuable pharmacological properties while being well tolerated.

In addition, the substances of the formula I are particularly suitable for use as intermediates which can be employed, in particular, for synthesizing inhibitors of the cellular $Na^+/H^+$ antiporter which are of the acylguanidine type, other than those of formula I.

The novel compounds are inhibitors of the cellular $Na^+/H^+$ antiporter, i.e. active compounds which inhibit the cellular $Na^+/H^+$ exchange mechanism (Düsing et al., Med. Klin. 87, 378–384 (1992)), and thus represent good antiarrhythmic agents which are particularly suitable for treating arrhythmias which arise as a result of lack of oxygen.

The active compound of the acylguanidine group which is most well-known is amiloride. However, this substance first and foremost exhibits hypotensive and saluretic effects, which are undesirable when treating disturbances of cardiac rhythm, in particular, whereas the antiarrhythmic properties are only very weakly expressed.

EP 04 16 499, for example, discloses compounds which are structurally similar.

The novel substances of the acylguanidine type, i.e., where Q is —N=C($NH_2$)$_2$, of the invention exhibit a good cardioprotective effect and are therefore particularly suitable for the treatment of infarction, for infarction prophylaxis and for treating angina pectoris. In addition, the substances counteract all types of pathological hypoxic and ischaemic damage, so that the disorders which are caused primarily or secondarily by such damage can be treated. The active compounds are also well suited for preventive applications.

Because of the protective effects of these substances in pathological hypoxic or ischaemic situations, there are further possibilities for using these substances in association with surgical interventions, for protecting organs which are from time to time less well supplied, in association with organ transplantations, for protecting the organs which are being removed, in association with angioplastic blood vessel or cardiac surgery, in association with ischaemias of the nervous system, in association with the therapy of conditions of shock, and for prophylactic prevention of essential hypertension.

In addition, the compounds can also be employed as therapeutic agents in diseases arising from cell proliferation, such as arteriosclerosis, late complications in diabetes, tumor diseases, in particular of the lung, liver and kidneys, and also organ hypertrophies and hyperplasias. In addition to this, these substances are also suitable for being used diagnostically for diagnosing disorders which are associated with an increased activity of the Na+/H+ antiporter, e.g. in erythrocytes, thrombocytes or leucocytes.

The effects of the compounds can be ascertained using methods which are known per se, as described, for example, by N. Escobales and J. Figueroa in J. Membrane Biol. 120, 41–49 (1991) or by L. Counillon, W. Scholz, H. J. Lang and J. Pouysségur in Mol. Pharmacol. 44, 1041–1045 (1993).

Examples of suitable experimental animals are mice, rats, guinea pigs, dogs, cats, monkeys or pigs.

The compounds of the formula I, in particular the acylguanidine derivatives, may, therefore, be used as pharmaceutically active compounds in human and veterinary medicine. In addition, all the compounds of formula I can be used as intermediates for preparing further pharmaceutically active compounds, in particular those which inhibit the cellular Na+/H+ antiporter.

The compounds may be used as pharmaceutical agents in a manner analogous to amiloride and other known acylguanidine compounds, but exhibiting the advantages described herein, e.g., they inhibit the cellular Na+/H+ exchange mechanism and show a high activity in treatment of disturbances of cardiac rhythm. As intermediates, the compounds may be used to prepare pharmaceutically active compounds using synthetic methods analogous to those known in the art.

The invention thus relates to ortho-substituted benzoic acid derivatives of the formula I and to their physiologically harmless salts.

In the given formulae, A is a branched or unbranched alkyl group having 1–6, preferably 1–4, in particular 1, 2 or 3, C atoms, specifically methyl and ethyl by preference, with propyl, isopropyl, butyl and isobutyl also being preferred, and sec-butyl, tert-butyl, pentyl, isopentyl (3-methylbutyl), hexyl or isohexyl (4-methylpentyl) furthermore being preferred.

$R^1$ is preferably A, with A having, in particular, the previously mentioned, particularly preferred meanings, and is also preferably OA, $CF_3$, Cl, Br, $NH_2$ or CN.

$R^2$ is particularly preferably $SO_2A$, $SO_2NH_2$ or $SO_2NA_2$.

$R^3$ is preferably halogen, such as F, in particular, however, Br or Cl; however, $R^3$ is also A, in particular methyl, CN or CHO.

$R^4$ and $R^5$ are preferably in each case, independently of one another, H or A.

If $R^4$ and $R^5$ are together alkylene, the alkylene group is preferably unbranched with $-(CH_2)_k-$, where k is 4 or 5, being specifically preferred; however, $-(CH_2)_2-O-(CH_2)_2-$, $-(CH_2)_2-NH-(CH_2)_2-$, $-(CH_2)_2-NA-(CH_2)_2-$, $-CH_2-O-(CH_2)_2-$, $-CH_2-NH-(CH_2)_2-$, or $-CH_2-NA-(CH_2)_2-$ or $-CO-(CH_2)_3-$, $-CO-(CH_2)_4-$ or $-CH_2-CO-(CH_2)_2$ are also preferred.

Ph is preferably phenyl which is unsubstituted or is substituted once by Cl, Br, A, OA, $NH_2$, NHA, $NA_2$ or $CF_3$.

$R^6$ is preferably A, in particular methyl, or else preferably also unsubstituted phenyl.

$R^7$ and $R^8$ are preferably, independently of one another, H.

The radical X is preferably O or NH.

Q is, in particular, $-N=C(NH_2)_2$, if the active compounds are those which possess good pharmacological properties.

In the case of intermediates which are particularly suitable for synthesizing pharmaceutical active compounds, Q is, in addition to guanidinyl, particularly preferably Cl, Br, OH or OA, and also $-O-CO-A$ or $-O-CO-Ph$.

Ac is preferably alkanoyl having from 1 to 6 C atoms, in particular formyl, acetyl, propionyl, butyryl, isobutyryl, valeroyl or capronyl, but also, preferably benzoyl, toluoyl or 1-naphthoyl or 2-naphthoyl.

As reactive esterified OH groups or leaving groups which are readily nucleophilically substituted included, for example, are $-O$-benzyl, $-O-CH_3$, $-OA$, $-O$-tolyl, $-O-SO_2-CH_3$, $-O-SO_2$-tolyl, $-O-SO_2-CF_3$, $-O-SO_2-CHF_2$ and additionally acyl groups such as phenoxyacetyl; alkoxycarbonyl, such as methoxycarbonyl, ethoxycarbonyl, 2,2,2,-trichloroethoxy-carbonyl, isopropoxycarbonyl, tert-butoxycarbonyl (CBOC) and 2-iodoethoxycarbonyl; aralkyloxycarbonyl, such as benzyloxycarbonyl (CBZ), 4-methoxybenzyloxycarbonyl and 9-fluorenylmethoxycarbonyl (FMOC) and protective hydroxyl groups such as tert-butyl, benzyl, p-nitrobenzoyl, p-toluenesulphonyl and acetyl, with benzyl and acetyl being particularly preferred.

It applies generally that all the radicals which occur several times in the compounds can be identical or different.

Accordingly, the invention relates, in particular, to those compounds of the formula I in which at least one of the said radicals has one of the previously mentioned preferred meanings. Some preferred groups of compounds can be expressed by the following formulae Ia to Ih, which conform to the formula I and in which the radicals which are not more precisely defined have the meaning given in association with formula I, in which, however, in Ia $R^1$ is A and $R^2$ is $-SO_2-CH_3$ or $-SO_2-NH_2$ or $-SO_2-NA_2$;

in Ib $R^1$ is A, Cl, Br, $NH_2$, OH or OA, and $R_2$ is $SO_2CH_3$;

in Ic $R^1$ is A, Cl or Br, and $R^3$ is CN, CHO, Cl or Br;

in Id $R^2$ is $SO_2-CH_3$, $-SO_2NH_2$ or $SO_2-NA_2$, and $R^3$ is A, F, Cl, Br or CN;

in Ie $R^1$ is A, $R^2$ is $-SO_2-CH_3$ and $R_3$ is A, F, Cl, Br or CN;

in If $R^1$ is A, $R^2$ is $-SO_2-NH_2$ or $-SO_2N(CH_3)_2$, and $R^3$ is A, F, Cl or Br;

in Ig $R^1$ is $CH_3$ or $C_2H_5$, $R^3$ is F, Cl, Br, CHO or COA, and $R^2$ is $-SO_2-CH_3$;

in Ih $R^1$ and $R^3$ are in each case, independently of one another, Hal, A or CN.

In addition, all those compounds are preferred in which the radicals $R^1$, $R^2$ and $R^3$ have the preferred meanings mentioned under Ia to Ih, but in which Q is simultaneously $-N=C(NH_2)_2$.

The invention also relates to a process for preparing ortho-substituted benzoic acid derivatives of the abovementioned formula I, and also the salts thereof, characterized in that a compound of the formula II

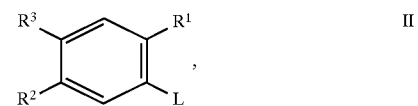

in which $R^1$, $R^2$ and $R^3$ have the given meanings, and L is $CH_3$, $CH_2OH$, CHO or phenyl, is converted by oxidation into a compound of the formula I, or in that a compound of the formula II, in which L is CN, is converted by hydrolysis into a compound of the formula I, or in that a compound of the formula II, in which $R^2$ is H and L is $CO_2R^5$, is converted by chlorosulphonation, followed by reduction and alkylation, into a compound of the formula I, or in that a compound of the formula I is liberated from one of its functional derivatives by treatment with a solvolyzing or hydrogenolyzing agent, or in that a benzoic acid derivative, which per se conforms to the formula I but in which one of the radicals $R^1$, $R^2$ or $R^3$ is missing, is converted by alkylation, acylation, halogenation or nitration into a compound of the formula I, or in that a radical $R^1$, $R^2$, $R^3$ and/or Q is transformed into another radical $R^1$, $R^2$, $R^3$ and/or Q by hydrolyzing an ester of the formula I, or esterifying a carboxylic acid of the formula I or converting it into an anhydride or acid halide or converting it into an acylguanidine, or catalytically hydrogenating a CN group, or hydrolyzing a nitrile group to form a carbamoyl group or an acid group, or transforming a nitrile group into a thiocarbamoyl group, and/or in that a compound of the formula I is converted into one of its salts by treatment with an acid or a base.

The compounds of the formula I are otherwise prepared by methods which are known per se, as described in the literature (e.g. in the standard works such as Houben-Weyl, Methoden der organischen Chemie, (Methods of Organic Chemistry), Georg-Thieme-Verlag, Stuttgart; Organic Reactions, John Wiley & Sons, Inc., New York; and also in the abovementioned patent application), and specifically under reaction conditions which are known for the said reactions and which are suitable for these reactions. In this context, use can also be made of variants which are known per se but which have not been mentioned in any detail here.

If desired, the starting compounds may also be formed in situ, such that they are not isolated from the reaction mixture but are instead immediately subjected to further reaction to form the compounds of the formula I.

The compounds of the formula I are, inter alia, preferably prepared by oxidizing a compound of the formula II in which L is $CH_3$, $CH_2OH$, CHO or phenyl.

Oxidation of methyl-substituted benzoic acid derivatives is achieved, for example, using nitric acid or using $KMnO_4$.

Primary alcohols of the formula II can be converted into the corresponding acids using, for example, AgO, KMnO$_4$, CrO$_3$ or other strong oxidizing agents which are known per se. It is furthermore possible to convert appropriately substituted benzaldehydes of the formula II into the corresponding acids, or their salts, using, for example, the customary oxidizing agents or else, for example, by means of the Cannizzaro reaction. It is also possible to convert the aldehydes of the formula II directly into the corresponding esters using Al(OC$_2$H$_5$)$_3$ for example. In addition, biphenyls having an appropriate substitution pattern can be converted into the corresponding carboxylic acids by oxidation with RuO$_4$.

The oxidations are always processes which are known per se, which processes are described, for example, in J. March, Adv. Org. Chem., 3rd ed., John Wiley & Sons (1985).

Compounds of the formula I may also be prepared by electrophilic substitution reactions on the aromatic moiety if other side reactions can be excluded. They may, for example, be chlorinated, brominated, alkylated or acylated under the conditions of the Friedel-Crafts reactions by reacting the appropriate halogen or alkyl chloride or alkyl bromide, while catalyzing with Lewis acids, such as, for example, AlCl$_3$, FeBr$_3$ or Fe, or the desired acyl chloride in the presence of a Lewis acid preferably at temperatures of from about 30° C. to 150° C., expediently 50° C. to 150° C., in an inert solvent such as, for example, hydrocarbons, THF, or carbon tetrachloride, with the compound of the formula I to be derivatized.

The compounds of the formula I can also be obtained by liberating them from their functional derivatives by means of solvolysis, in particular hydrolysis, or by means of hydrogenolysis.

Starting compounds which are particularly preferred for the hydrolysis are compounds of the formula I which possess a nitrile group or those of the formula II in which L is CN. Compounds of this nature can be hydrolyzed to give the carboxylic acid under reaction conditions which are known per se, for example in a medium containing sulphuric acid, by way of the corresponding carboxamide derivative, or generally by means of heating together with strong acids or bases.

Further preferred starting compounds for the solvolysis or hydrogenolysis are those which, in place of one or more free amino groups and/or hydroxyl groups, contain corresponding, protected amino groups and/or hydroxyl groups, but which otherwise conform to the formula I, preferably those which carry an amino protective group in place of an H atom which is bonded to an N atom, in particular those which carry an R'-N group, in which R' is an amino protective group, in place of an HN group, and/or those which carry an hydroxyl protective group in place of the H atom of an hydroxyl group, for example those which carry a —COOR" group, in which R" is an hydroxyl protective group, in place of a —COOH group, but which conform to the formula I.

Several identical or different—protected amino groups and/or hydroxyl groups may also be present in the molecule of the starting compound. If the protective groups which are present differ from each other, they can in many cases be eliminated selectively.

The term "amino protective group" is well known and refers to groups which are suitable for protecting (for blocking) an amino group against chemical reactions but which can readily be removed once the desired chemical reaction has been carried out at another site in the molecule. Unsubstituted or substituted acyl, aryl (e.g. 2,4-dinitrophenyl (DNP)), aralkoxymethyl (e.g. benzyloxymethyl (BOM)) or aralkyl groups (e.g. benzyl, 4-nitrobenzyl and triphenylmethyl) are especially typical of such groups. Since the amino protective groups are removed after the desired reaction (or sequence of reactions) is completed, their nature and size is otherwise not critical; nevertheless, those having 1–20, in particular 1–8, C atoms are preferred. In connection with the present process, the term "acyl group" is to be interpreted in the widest possible sense. It embraces acyl groups which are derived from aliphatic, araliphatic, aromatic or heterocyclic carboxylic acids or sulphonic acids, such as, in particular, alkoxycarbonyl, aryloxycarbonyl and, especially, aralkoxycarbonyl groups. Examples of acyl groups of this nature are alkanoyl, such as acetyl, propionyl and butyryl; aralkanoyl, such as phenylacetyl; aroyl such as benzoyl or toluoyl; aryloxyalkanoyl, such as phenoxyacetyl; alkoxycarbonyl, such as methoxycarbonyl, ethoxycarbonyl, 2,2,2-trichloroethoxycarbonyl, isopropoxycarbonyl, tert-butoxycarbonyl (BOC) and 2-iodoethoxycarbonyl; aralkyloxycarbonyl, such as benzyloxycarbonyl (CBZ), 4-methoxybenzyloxycarbonyl and 9-fluorenylmethoxycarbonyl (FMOC). Those amino protective groups which are preferred are BOC, DNP and BOM, and also CBZ, benzyl and acetyl.

The term "hydroxyl protective group" is likewise well known and refers to groups which are suitable for protecting an hydroxyl group against chemical reactions but which can readily be removed once the desired chemical reaction has been carried out at another site in the molecule. The above-mentioned unsubstituted or substituted aryl, aralkyl or acyl groups, and also alkyl groups, are typical of such groups. The nature and size of the hydroxyl protective groups is not critical since they are removed once again after the desired chemical reaction or sequence of reactions has been completed; groups having 1–20, in particular 1–10, C atoms are preferred. Some examples of hydroxyl protective groups are tert-butyl, benzyl, p-nitrobenzoyl, p-toluenesulphonyl and acetyl, with benzyl and acetyl being particularly preferred.

The functional derivatives of the compounds of the formula I, which derivatives are to be used as starting compounds, can be prepared by customary methods, as described, for example, in the said standard works and patent applications, for example by reacting compounds which conform to the formulae I or II, with, however, at least one of these compounds containing a protective group in place of an H atom.

Depending on the protective group employed, the liberation of the compounds of the formula I from their functional derivatives is achieved, for example, using strong acids, expediently using trifluoroacetic acid or perchloric acid, or else using other strong inorganic acids, such as hydrochloric acid or sulphuric acid, or using strong organic carboxylic acids, such as trichloroacetic acid, or sulphonic acids, such as benzenesulphonic acid or p-toluenesulphonic acid. While it is possible for an additional, inert solvent to be present, this is not always necessary.

Organic solvents are preferably used as inert solvents, for example carboxylic acids, such as acetic acid, ethers, such as tetrahydrofuran (THF) or dioxane, amides, such as dimethylformamide (DMF), halogenated hydrocarbons, such as dichloromethane, and also alcohols, such as methanol, ethanol or isopropanol, and also water. Mixtures of the above-mentioned solvents are also suitable. Trifluoroacetic acid is preferably used in excess without the addition of any further solvent, while perchloric acid is used in the form of a mixture consisting of acetic acid and 70% perchloric acid in a ratio of 9:1. The reaction temperatures for the cleavage are expediently from about 0° C. to about 50° C.; the reaction is preferably carried out at from 15° C. to 30° C. (room temperature).

The BOC group can, for example, preferably be eliminated using 40% trifluoroacetic acid in dichloromethane or using approximately 3 to 5N HCl in dioxane at 15°–60°, while the FMOC group can be eliminated using an approximately 5–20% solution of dimethylamine, diethylamine or piperidine in DMF at 15°–50° C. The DNP group is also eliminated, for example, using an approximately 3–10% solution of 2-mercaptoethanol in DMF/water at 15°–30° C.

Protective groups (e.g. BOM, CBZ or benzyl) which can be removed by hydrogenolysis can be eliminated, for example, by being treated with hydrogen in the presence of a catalyst (e.g. of a precious metal catalyst such as palladium, expediently on a support such as carbon). The abovementioned solvents, in particular, for example, alcohols, such as methanol or ethanol, or amides, such as DMF, are suitable as solvents in this context. As a rule, the hydrogenolysis is carried out at temperatures of from about 0° C. to 100° C. and under pressures of from about 1 to 200 bar, preferably at 20°–30° C. and at 1–10 bar. Hydrogenolysis of the CBZ group is readily achieved, for example, on 5–10% Pd-C in methanol at 20°–30° C.

Furthermore, a radical $R^1$, $R^2$, $R^3$ and/or Q in a compound of the formula I can be transformed into (an)other radical(s) $R^1$, $R^2$, $R^3$ and/or Q.

For example, it is possible for an ester of the formula I (Q=OA) to be hydrolyzed, expediently by means of solvolysis, using a method which is known per se, for example with NaOH or KOH in dioxane/water at temperatures of from −40° C., preferably 10°–30° C.

Cyano groups can furthermore be reduced to aminomethyl groups. Reduction of cyano groups to aminomethyl groups is expediently achieved by catalytic hydrogenation, for example on Raney Nickel at temperatures of from about 0°–100° C., preferably 10°–30° C., and under pressures of from about 1–200 bar, preferably at standard pressure, in an inert solvent, for example in a lower alcohol such as methanol or ethanol, expediently in the presence of ammonia. If, for example, the reaction is carried out at approximately 20° C. and 1 bar, benzyl ester groups or N-benzyl groups which are present in the starting material are preserved. If it is desired to cleave the latter hydrogenolytically, a precious metal catalyst, preferably Pd-charcoal, is expediently used, it being possible to add an acid such as acetic acid and also water to the solution.

For esterification, an acid of the formula I can be treated with an excess of an alcohol, expediently in the presence of a strong acid, such as hydrochloric acid or sulphuric acid, and at temperatures of from about 0°–100° C., preferably 20°–50° C.

It is also possible to convert a nitrile group into a thiocarbamoyl group by reaction with hydrogen sulphide, expediently at temperatures of from about −10°–+50° C., using reaction times of from a few minutes to 3 days, in suitable solvents or solvent mixtures, with $H_2S$ gas being passed in continuously.

Suitable solvents are also, in particular, alcohols, such as methanol, ethanol, isopropanol, n-butanol or tert-butanol; ethers, such as diethyl ether, diisopropyl ether, tetrahydrofuran (THF) or dioxane; glycol ethers, such as ethylene glycol monomethyl ether or ethylene glycol monoethyl ether (methyl glycol or ethyl glycol), or ethylene glycol dimethyl ether (diglyme); ketones, such as acetone or butanone; nitriles, such as acetonitrile; nitro compounds, such as nitromethane or nitrobenzene; esters, such as ethyl acetate or hexamethylphosphoric triamide; sulphoxides, such as dimethyl sulphoxide (DMSO); chlorinated hydrocarbons, such as dichloromethane, chloroform, trichloroethylene, 1,2-dichloroethane or carbon tetrachloride; hydrocarbons, such as benzene, toluene or xylene. Mixtures of these solvents with each other are also suitable. Those solvents which are particularly suitable are pyridine, triethylamine or DMF, or mixtures of these solvents.

In addition, a suitable compound of the formula I, in which Q is not guanidinyl, can be converted into an acylguanidine by reaction with guanidine.

The reaction of a reactive carboxylic acid derivative of the formula II with guanidine is effected in a manner known per se, preferably in a protic or aprotic, polar or nonpolar, inert organic solvent.

Suitable solvents are methanol, THF, dimethoxy-ethane, dioxane, or mixtures which can be prepared therefrom, and also water. Suitable reaction temperatures are, for example, temperatures of from 20° C. to the boiling point of the solvent. The reaction times are from about 5 min to 12 h. It is expedient to add an acid capturing agent during the reaction. Any type of base which does not interfere with the reaction itself is suitable for this purpose. However, that which is particularly suitable is the use of inorganic bases such as potassium carbonate or of organic bases such as triethylamine or pyridine, or else an excess of guanidine.

A base of the formula I can be converted into the affiliated acid addition salt using an acid. Acids which are suitable for this reaction are in particular those which give rise to physiologically harmless salts. Thus, use can be made of inorganic acids, for example sulphuric acid, nitric acid, hydrohalic acids, such as hydrochloric acid or hydrobromic acid, phosporic acids, such as orthophosphoric acid, or sulphamic acid, and also of organic acids, in particular aliphatic, alicyclic, araliphatic, aromatic or heterocyclic monobasic or polybasic carboxylic acids, sulphonic acids or sulphuric acids, e.g. formic acid, acetic acid, trifluoroacetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulphonic acid, ethanesulphonic acid, ethanedisulphonic acid, 2-hydroxyethanesulphonic acid, benzenesulphonic acid, p-toluenesulphonic acid, naphthalene monosulphonic and disulphonic acids or laurylsulphuric acid. Salts with acids which are not physiologically harmless, e.g. picrates, may be used for isolating and/or purifying the compounds of the formula I.

If desired, the free bases of the formula I may be liberated from their salts, for example by treatment with strong bases, such as sodium hydroxide, potassium hydroxide, sodium carbonate or potassium carbonate.

The compounds of the formula I and their physiologically harmless salts may be used to produce pharmaceutical preparations, especially by a non-chemical route. When being used for this purpose, they can be brought, together with at least one solid, liquid and/or semiliquid carrier substance or auxiliary substance and, where appropriate, in combination with one or more additional active compound (s), into a suitable dosage form.

The invention furthermore relates to compositions, in particular pharmaceutical preparations, which contain at least one compound of the formula I, in which Q is guanidinyl, and/or one of its physiologically harmless salts.

These preparations can be used as medicaments in human or veterinary medicine. Suitable carrier substances are organic or inorganic substances which are suitable for enteral (e.g. oral), parenteral or topical administration and which do not react with the novel compounds, for example water, vegetable oils, benzyl alcohols, polyethylene glycols, glycerol triacetate, gelatin, carbohydrates, such as lactose or starch, magnesium stearate, talc, lanolin or vaseline. For oral application, use is made, in particular, of tablets, coated tablets, capsules, syrups, juices or drops, for rectal application of suppositories, for parenteral application of solutions, preferably oily or aqueous solutions, and also of suspensions, emulsions or implants, and for topical application of ointments, creams, pastes, lotions, gels, sprays, foams, aerosols, solutions (e.g. solutions in alcohols, such as ethanol or isopropanol, acetonitrile, DMF, dimethylacetamide or 1,2-propanediol, or their mixtures with each other and/or with water) or powders. The novel compounds can also be lyophilized and the resulting lyophilisates used, for example, to produce preparations for injection.

Liposomal preparations are also especially suitable for topical application. The given preparations can be sterilized and/or contain auxiliary substances such as glidants, preservatives, stabilizers and/or wetting agents, emulsifiers, salts for influencing the osmotic pressure, buffering substances, coloring substances, flavoring substances and/or aromatizing substances. They can, if desired, also contain one or more additional active compounds, e.g. one or more vitamins.

The compounds of the formula I, and their physiologically harmless salts, can be administered to humans or animals, in particular mammals such as monkeys, dogs, cats, rats or mice, and be used for the therapeutic treatment of the human or animal body and also in the control of diseases, in particular in association with the therapy and/or prophylaxis of disturbances of the cardiovascular system. They are suitable, therefore, for the treatment of arrhythmias, in particular when the latter are caused by a lack of oxygen, angina pectoris, infarctions, ischaemias of the nervous system, such as, for example, stroke or cerebral oedemas, and conditions of shock, and also for preventive treatment.

The substances can also be employed as therapeutic agents in diseases in which cell proliferation plays a role, such as arteriosclerosis, late complications in diabetes, tumor diseases, fibroses and organ hypertrophies and hyperplasias.

In this context, the substances according to the invention maybe administered in analogy with known anti-arrhythmics, e.g. aprindine, preferably in doses of from about 0.01–5 mg, in particular from about 0.02–0.5 mg per dosage unit. The daily dose is preferably between about 0.0001 and 0.1, in particular between 0.0003 and 0.001, mg/kg of body weight. However, the special dose for each particular patient depends on a wide variety of factors, for example on the activity of the special compound employed, on the age, on the body weight, on the general state of health, on the sex, on the diet, on the time and route of administration, on the speed of excretion, on the combination of medicines being employed, and on the severity of the particular disease to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding German application P4430212.6, are hereby incorporated by reference.

In the examples which follow, "customary workingup" denotes":

If required, water is added and extraction takes place using an organic solvent such as ethyl acetate; the organic phase is separated off and dried over sodium sulphate, after which it is filtered and evaporated; the residue is purified by chromatography and/or crystallization.

EXAMPLE 1

A solution of 200 g of 4-chloro-2-methylbenzoic acid and 410 g of chlorosulphonic acid is stirred at 140° for 6 h, and the reaction mixture is then poured onto ice. The precipitate is filtered off with suction and introduced in portions into a suspension of 447 g of sodium sulphite in 1170 ml of water at 10°, with a sodium hydroxide solution being added simultaneously so that a pH of 9 is achieved. The mixture is stirred for a further 3 h and then acidified while cooling with ice. The resulting precipitate is filtered off with suction once again and introduced, together with 610 g of methyliodide, into a mixture of 575 ml of methanol and 350 ml of water. The mixture is adjusted to a pH of 9 and boiled for 36 h, prior to the solvent being removed and workingup taking place in the customary manner. Methyl 2-methyl-4-chloro-5-methylsulphonylbenzoate is obtained, m.p. 151°.

The following are obtained in an analogous manner by reaction with chlorosulphonic acid, reduction and methylation from 2-ethyl-4-chlorobenzoic acid, methyl 2-ethyl-4-chloro-5-methylsulphonylbenzoate, m.p. 98°–100°;

from 2,4-dichlorobenzoic acid, methyl 2,4-dichloro-5-methylsulphonylbenzoate, m.p. 155°–156°;

from 2-methyl-4-bromobenzoic acid, methyl 2-methyl-4-bromo-5-methylsulphonylbenzoate, m.p. 150°;

from 2-bromo-4-methylbenzoic acid, methyl 2-bromo-4-methyl-5-methylsulphonylbenzoate, m.p. 160°–165°;

from 2-ethyl-4-bromobenzoic acid, methyl 2-ethyl-4-bromo-5-methylsulphonylbenzoate;

from 2-ethyl-4-chlorobenzoic acid, methyl 2-ethyl-4-chloro-5-methylsulphonylbenzoate;

from 2-ethyl-4,5-fluorobenzoic acid, methyl 2-ethyl-4,5-methylsulphonylfluorobenzoate;

from 2-chloro-4-fluorobenzoic acid, methyl 2-chloro-4-fluoro-5-methylsulphonylbenzoate, m.p. 137°–138°;

from 2-methoxy-4-chlorobenzoic acid, methyl 2-methoxy-4-chloro-5-methylsulphonylbenzoate;

from 2-fluoromethyl-4-chlorobenzoic acid, methyl 2-fluoromethyl-4-chloro-5-methylsulphonylbenzoate;

from 2-difluoromethyl-4-chlorobenzoic acid, methyl 2-difluoromethyl-4-chloro-5-methylsulphonylbenzoate;

from 2-ethynyl-4-bromobenzoic acid, methyl 2-ethynyl-4-bromo-5-methylsulfonylbenzoate;

from 2-ethynyl-4-methylbenzoic acid, methyl 2-ethynyl-4-methyl-5-methylsulphonylbenzoate;

from 2-nitro-4-fluorobenzoic acid, methyl 2-nitro-4-fluoro-5-methylsulphonylbenzoate;

from 2-methoxy-4-formylbenzoic acid, methyl 2-methoxy-4-formyl-5-methylsulphonylbenzoate;

from 2-difluoromethyl-4-formylbenzoic acid, methyl 2-difluoromethyl-4-formyl-5-methylsulphonylbenzoate;

from 2-ethynyl-4-chlorobenzoic acid, methyl 2-ethynyl-4-chloro-5-methylsulphonylbenzoate;

from 2-cyano-4-methylbenzoic acid, methyl 2-cyano-4-methyl-5-methylsulphonylbenzoate;

from 2-pentafluoroethyl-4-fluorobenzoic acid, methyl 2-pentafluoroethyl-4-fluoro-5-methylsulphonylbenzoate;

from 2-methyl-4-fluorobenzoic acid, methyl 2-methyl-4-fluoro-5-methylsulphonylbenzoate;

from 2-cyano-4-formylbenzoic acid, methyl 2-cyano-4-formyl-5-methylsulphonylbenzoate.

EXAMPLE 2

10 g of methyl 2-methyl-4-chloro-5-methylsulphonylbenzoate are added, while cooling with ice, to a mixture of 30 ml of conc. HCl and 200 ml of methanol, and the whole is then stirred for 2 h. The resulting precipitate is filtered off with suction and recrystallized from methanol. 2-Methyl-4-chloro-5-methylsulphonylbenzoic acid is obtained, m.p. 217°–218°.

The following are obtained in an analogous manner by hydrolysis from methyl 2-ethyl-4-chloro-5-methylsulphonylbenzoate: 2-ethyl-4-chloro-5-methylsulphonylbenzoic acid, m.p. 180°–183°;

from methyl 2,4-dichloro-5-methylsulphonylbenzoate: 2,4-dichloro-5-methylsulphonylbenzoic acid, m.p. 208°;

from methyl 2-methyl-4-bromo-5-methylsulphonylbenzoate: 2-methyl-4-bromo-5-methylsulphonylbenzoic acid, m.p. 221°–222°;

from methyl 2-bromo-4-methyl-5-methylsulphonylbenzoate: 2-bromo-4-methyl-5-methylsulphonylbenzoic acid, m.p. 209°–212°;

from methyl 2-chloro-4-fluoro-5-methylsulphonylbenzoate: 2-chloro-4-fluoro-5-methylsulphonylbenzoic acid, m.p. 213°–215°;

from methyl 2-methoxy-4-chloro-5-methylsulphonylbenzoate: 2-methoxy-4-chloro-5-methylsulphonylbenzoic acid, m.p. 236°–237°;

from methyl 2-fluoromethyl-4-chloro-5-methylsulphonyl benzoate; 2-fluoromethyl-4-chloro-5-methylsulphonylbenzoic acid;

from methyl 2-ethyl-4-bromo-5-methylsulphonylbenzoate: 2-ethyl-4-bromo-5-methylsulphonylbenzoic acid;

from methyl 2-methyl-4-fluoro-5-methylsulphonylbenzoate: 2-methyl-4-fluoro-5-methylsulphonylbenzoic acid;

from methyl 2-ethyl-4-fluoro-5-methylsulphonylbenzoate: 2-ethyl-4-fluoro-5-methylsulphonylbenzoic acid;

from methyl 2-difluoromethyl-4-chloro-5-methylsulphonyl benzoate: 2-difluoromethyl-4-chloro-5-methylsulphonylbenzoic acid;

from methyl 2-ethynyl-4-bromo-5-methylsulphonylbenzoate: 2-ethynyl-4-bromo-5-methylsulphonylbenzoic acid;

from methyl 2-ethynyl-4-methyl-5-methylsulphonylbenzoate: 2-ethynyl-4-methyl-5-methylsulphonylbenzoic acid;

from methyl 2-nitro-4-fluoro-5-methylsulphonylbenzoate: 2-nitro-4-fluoro-5-methylsulphonylbenzoic acid;

from methyl 2-methoxy-4-formyl-5-methylsulphonylbenzoate: 2-methoxy-4-formyl-5-methylsulphonylbenzoic acid;

from methyl 2-difluoromethyl-4-formyl-5-methylsulphonyl benzoate: 2-difluoromethyl-4-formyl-5-methylsulphonylbenzoic acid;

from methyl 2-ethynyl-4-chloro-5-methylsulphonylbenzoate: 2-ethynyl-4-chloro-5-methylsulphonylbenzoic acid;

from methyl 2-gyano-4-methyl-5-methylsulphonylbenzoate: 2-cyano-4-methyl-5-methylsulphonylbenzoic acid;

from methyl 2-pentafluoroethyl-4-fluoro-5-methylsulphonylbenzoate: 2-pentafluoroethyl-4-fluoro-5-methylsulphonylbenzoic acid;

from methyl 2-cyano-4-formyl-5-methylsulphonylbenzoate: 2-cyano-4-formyl-5-methylsulphonylbenzoic acid.

EXAMPLE 3

15 g of methyl 2-ethyl-4-chloro-5-methylsulphonylbenzoate are stirred, at room temperature for 1 h, in 100 ml of methanol and 50 ml of 2N sodium hydroxide solution. The reaction mixture is then concentrated, and 200 ml of ice water are added. After the mixture has been acidified with conc. HCl, the resulting precipitate is filtered off with suction, washed with ether and dried. 2-Ethyl-4-chloro-5-methylsulphonylbenzoic acid is obtained, m.p. 180°–183°.

EXAMPLE 4

2 g of 1-chloro-2-methylsulphonyl-4,5-dimethylbenzene [obtainable in accordance with Ex. 1, proceeding from 1-chloro-3,4-dimethylbenzene, which is reacted with chlorosulphonic acid, sodium sulphite and methyl iodide] are heated at 132° for 5 h in an autoclave together with 40 ml of 15% nitric acid. The reaction mixture is then extracted with ethyl acetate and worked up in the customary manner. 2-Methyl-4-chloro-5-methylsulphonylbenzoic acid is obtained, m.p. 217°–218°.

EXAMPLE 5

8.3 g of 2-methyl-4-chloro-5-methylsulphonylbenzoic acid are mixed together with 70 ml of N-methylpyrrolidone and 7.4 g of CuCN, and the whole is stirred at 150° for 3 days. The reaction mixture is then poured into 250 ml of water and working-up takes place in the customary manner. After recrystallization from methanol, 2-methyl-4-cyano-5-methylsulphonylbenzoic acid is obtained, m.p. 248°–249°.

The following are obtained in an analogous manner by reaction of CuCN with 2-ethyl-4-chloro-5-methylsulphonylbenzoic acid: 2-ethyl-4-cyano-5-methylsulphonylbenzoic acid;

with 2,4-dichloro-5-methylsulphonylbenzoic acid: 2,4-dicyano-5-methylsulphonylbenzoic acid;

with 2-chloro-4-fluoro-5-methylsulphonylbenzoic acid: 2-chloro-4-cyano-5-methyloulphonylbenzoic acid;

with 2-methoxy-4-chloro-5-methylsulphonylbenzoic acid: 2-methoxy-4-cyano-5-methylsulphonylbenzoic acid;

with 2-fluoromethyl-4-chloro-5-methylsulphonylbenzoic acid: 2-fluoromethyl-4-cyano-5-methylsulphonylbenzoic acid;

with 2-difluoromethyl-4-chloro-5-methylsulphonylbenzoic acid: 2-difluoromethyl-4-cyano-5-methylsulphonylbenzoic acid;

with 2-ethynyl-4-chloro-5-methylsulphonylbenzoic acid: 2-ethynyl-4-cyano- 5-methylsulphonylbenzoic acid;

with 2-pentafluoroethyl-4-chloro-5-methylsulphonylbenzoic acid: 2-pentafluoroethyl-4-cyano-5-methylsulphonylbenzoic acid.

EXAMPLE 6

50 g of 2,4-dichloro-5-methylsulphonylbenzoic acid [obtainable in accordance with Ex. 2] are heated in an autoclave, at 180° and under a pressure of 30 bar for 12 h, together with 500 ml of a 32% aqueous solution of ammonia. The reaction mixture is then poured onto ice, acidified with conc. HCl and extracted by boiling with methanol. 2-Amino-4-chloro-5-methylsulphonylbenzoic acid is obtained, m.p. 284°–286°.

EXAMPLE 7

5.8 g of 2-bromo-4-fluoro-5-methylsulphonylbenzoic acid are stirred, at room temperature for 12 h, in 20 ml of DMF together with 3.7 ml of methyl iodide and 8.3 g of potassium carbonate. The reaction mixture is then concentrated and 50 ml of water are added to it. The resulting precipitate is filtered off with suction and dried. Methyl 2-bromo-4-fluoro-5-methylsulphonylbenzoate is obtained, m.p. 126°.

EXAMPLE 8

74.1 g of 2-methyl-4-bromo-5-chlorosulphonylbenzoic acid [obtainable by reacting 2-methyl-4-bromobenzoic acid with chlorosulphonic acid] are stirred, at 10° and over a period of 1.5 h, into 170 ml of a 32% aqueous solution of ammonia, and this mixture is subsequently stirred at room temperature for 3 h. After that, the reaction mixture is concentrated, 50 ml of water are added, and this mixture is acidified with conc. HCl. The resulting precipitate is filtered off with suction and recrystallized from methanol. 2-Methyl-4-bromo-5-aminosulphonylbenzoic acid is obtained, m.p. 237°.

The following are obtained in an analogous manner by reacting ammonia with 2-ethyl-4-bromo-5-chlorosulphonylbenzoic acid, 2-ethyl-4-bromo-5-aminosulphonylbenzoic acid;

with 2-propyl-4-bromo-5-chlorosulphonylbenzoic acid, 2-propyl-4-bromo-5-aminosulphonylbenzoic acid;

with 2-isopropyl-4-chloro-5-chlorosulphonylbenzoic acid, 2-isopropyl-4-chloro-5-aminosulphonylbenzoic acid;

with 2-propyl-4-fluoro-5-chlorosulphonylbenzoic acid, 2-propyl-4-fluoro-5-aminosulphonylbenzoic acid;

with 2-methoxy-4-bromo-5-chlorosulphonylbenzoic acid, 2-methoxy-4-bromo-5-aminosulphonylbenzoic acid;

with 2-cyano-4-chloro-5-chlorosulphonylbenzoic acid, 2-cyano-4-chloro-5-aminosulphonylbenzoic acid;

with 2-isopropyl-4-fluoro-5-chlorosulphonylbenzoic acid, 2-isopropyl-4-fluoro-5-aminosulphonylbenzoic acid;

with 2-butyl-4-fluoro-5-chlorosulphonylbenzoic acid, 2-butyl-4-fluoro-5-aminosulphonylbenzoic acid;

with 2-ethyl-4-fluoro-5-chlorosulphonylbenzoic acid, 2-ethyl-4-fluoro-5-aminosulphonylbenzoic acid;

with 2-nitro-4-bromo-5-chlorosulphonylbenzoic acid, 2-nitro-4-bromo-5-aminosulphonylbenzoic acid;

with 2-ethynyl-4-chloro-5-chlorosulphonylbenzoic acid, 2-ethynyl-4-chloro-5-aminosulphonylbenzoic acid;

with 2-trifluoromethyl-4-fluoro-5-chlorosulphonylbenzoic acid, 2-trifluoromethyl-4-fluoro-5-aminosulphonylbenzoic acid;

with 2-fluoromethyl-4-bromo-5-chlorosulphonylbenzoic acid, 2-fluoromethyl-4-bromo-5-aminosulphonylbenzoic acid;

with 2-fluoromethyl-4-formyl-5-chlorosulphonylbenzoic acid, 2-fluoromethyl-4-formyl-5-aminosulphonylbenzoic acid;

with 2-difluoromethyl-4-bromo-5-chlorosulphonylbenzoic acid, 2-difluoromethyl-4-bromo-5-aminosulphonylbenzoic acid;

with 2-pentafluoroethyl-4-chloro-5-chlorosulphonylbenzoic acid, 2-pentafluoroethyl-4-chloro-5-aminosulphonylbenzoic acid;

with 2-pentafluoroethyl-4-fluoro-5-chlorosulphonylbenzoic acid, 2-pentafluoroethyl-4-fluoro-5-aminosulphonylbenzoic acid.

EXAMPLE 9

7 g of 2-methyl-4-bromo-5-aminosulphonylbenzoic acid [obtainable in accordance with Ex. 8] are boiled for 5 h in a methanolic solution of HCl. The reaction mixture is then cooled down to room temperature, concentrated and worked up in the customary manner. After recrystallization has taken place from methanol, methyl 2-methyl-4-bromo-5-aminosulphonylbenzoate is obtained, m.p. 198°–200°.

The following are obtained in an analogous manner by esterifying the compounds from Example 8 with methanol:

methyl 2-ethyl-4-bromo-5-aminosulphonylbenzoate;

methyl 2-propyl-4-bromo-5-aminosulphonylbenzoate;

methyl 2-isopropyl-4-chloro-5-aminosulphonylbenzoate;

methyl 2-propyl-4-fluoro-5-aminosulphonylbenzoate;

methyl 2-methoxy-4-bromo-5-aminosulphonylbenzoate;

methyl 2-cyano-4-chloro-5-aminosulphonylbenzoate;

methyl 2-isopropyl-4-fluoro-5-aminosulphonylbenzoate;

methyl 2-butyl-4-fluoro-5-aminosulphonylbenzoate;

methyl 2-ethyl-4-fluoro-5-aminosulphonylbenzoate;

methyl 2-nitro-4-bromo-5-aminosulphonylbenzoate;

methyl 2-ethynyl-4-chloro-5-aminosulphonylbenzoate;

methyl 2-trifluoromethyl-4-fluoro-5-aminosulphonylbenzoate;

methyl 2-fluoromethyl-4-bromo-5-aminosulphonylbenzoate;

methyl 2-fluoromethyl-4-formyl-5-aminosulphonylbenzoate;

methyl 2-difluoromethyl-4-bromo-5-aminosulphonylbenzoate;

methyl 2-pentafluoroethyl-4-chloro-5-aminosulphonylbenzoate;

methyl 2-pentafluoroethyl-4-fluoro-5-aminosulphonylbenzoate.

EXAMPLE 10

The following are obtained, in analogy with Example 8, by reacting dimethylamine with 2-ethyl-4-bromo-5-chlorosulphonylbenzoic acid, 2-ethyl-4-bromo-5-N,N-dimethylaminosulphonylbenzoic acid;

with 2-propyl-4-bromo-5-chlorosulphonylbenzoic acid, 2-propyl-4-bromo-5-N,N-dimethylaminosulphonylbenzoic acid;

with 2-isopropyl-4-chloro-5-chlorosulphonylbenzoic acid, 2-isopropyl-4-chloro-5-N,N-dimethylaminosulphonylbenzoic acid;

with 2-propyl-4-fluoro-5-chlorosulphonylbenzoic acid, 2-propyl-4-fluoro-5-N,N-dimethylaminosulphonylbenzoic acid;

with 2-methoxy-4-bromo-5-chlorosulphonylbenzoic acid, 2-methoxy-4-bromo-5-N,N-dimethylaminosulphonylbenzoic acid;

with 2-cyano-4-chloro-5-chlorosulphonylbenzoic acid, 2-cyano-4-chloro-5-N,N-dimethylaminosulphonylbenzoic acid;

with 2-isopropyl-4-fluoro-5-chlorosulphonylbenzoic acid, 2-isopropyl-4-fluoro-5-N,N-dimethylaminosulphonylbenzoic acid;

with 2-butyl-4-fluoro-5-chlorosulphonylbenzoic acid, 2-butyl-4-fluoro-5-N,N-dimethylaminosulphonylbenzoic acid;

with 2-ethyl-4-fluoro-5-chlorosulphonylbenzoic acid, 2-ethyl-4-fluoro-5-N,N-dimethylaminosulphonylbenzoic acid;

with 2-nitro-4-bromo-5-chlorosulphonylbenzoic acid, 2-nitro-4-bromo-5-N,N-dimethylaminosulphonylbenzoic acid;

with 2-ethynyl-4-chloro-5-chlorosulphonylbenzoic acid, 2-ethynyl-4-chloro-5-N,N-dimethylaminosulphonylbenzoic acid;

with 2-trifluoromethyl-4-fluoro-5-chlorosulphonylbenzoic acid, 2-trifluoromethyl-4-fluoro-5-N,N-dimethylaminosulphonylbenzoic acid;

with 2-fluoromethyl-4-bromo-5-chlorosulphonylbenzoic acid, 2-fluoromethyl-4-bromo-5-N,N-dimethylaminosulphonylbenzoic acid;

with 2-fluoromethyl-4-formyl-5-chlorosulphonylbenzoic acid, 2-fluoromethyl-4-formyl-5-N,N-dimethylaminosulphonylbenzoic acid;

with 2-difluoromethyl-4-bromo-5-chlorosulphonylbenzoic acid, 2-difluoromethyl-4-bromo-5-N,N-dimethylaminosulphonylbenzoic acid;

with 2-pentafluoroethyl-4-chloro-5-chlorosulphonylbenzoic acid, 2-pentafluoroethyl-4-chloro-5-N,N-dimethylaminosulphonylbenzoic acid;

with 2-pentafluoroethyl-4-fluoro-5-chlorosulphonylbenzoic acid, 2-pentafluoroethyl-4-fluoro-5-N,N-dimethylaminosulphonylbenzoic acid.

EXAMPLE 11

The following are obtained, in analogy with Example 9, by esterifying the compounds from Example 10 with methanol:

methyl 2-ethyl-4-bromo-5-N,N-dimethylaminosulphonylbenzoate;

methyl 2-propyl-4-bromo-5-N,N-dimethylaminosulphonylbenzoate;

methyl 2-isopropyl-4-chloro-5-N,N-dimethylaminosulphonylbenzoate;

methyl 2-propyl-4-fluoro-5-N,N-dimethylaminosulphonylbenzoate;

methyl 2-methoxy-4-bromo-5-N,N-dimethylaminosulphonylbenzoate;

methyl 2-cyano-4-chloro-5-N,N-dimethylaminosulphonylbenzoate;

methyl 2-isopropyl-4-fluoro-5-N,N-dimethylaminosulphonylbenzoate;

methyl 2-butyl-4-fluoro-5-N,N-dimethylaminosulphonylbenzoate;

methyl 2-ethyl-4-fluoro-5-N,N-dimethylaminosulphonylbenzoate;

methyl 2-nitro-4-bromo-5-N,N-dimethylaminosulphonylbenzoate;

methyl 2-ethynyl-4-chloro-5-N,N-dimethylaminosulphonylbenzoate;

methyl 2-trifluoromethyl-4-fluoro-5-N,N-dimethylaminosulphonylbenzoate;

methyl 2-fluoromethyl-4-bromo-5-N,N-dimethylaminosulphonylbenzoate;

methyl 2-fluoromethyl-4-formyl-5-N,N-dimethylaminosulphonylbenzoate;

methyl 2-difluoromethyl-4-bromo-5-N,N-dimethylaminosulphonylbenzoate;

methyl 2-pentafluoroethyl-4-chloro-5-N,N-dimethylaminosulphonylbenzote;

methyl 2-pentafluoroethyl-4-fluoro-5-N,N-dimethylaminosulphonylbenzoate.

EXAMPLE 12

1.0 g of 2-methyl-4-cyano-5-methylsulphonylbenzoic acid [obtainable in accordance with Ex. 5] is dissolved in 15 ml of 1-methylpyrrolidone, and 0.67 g of 1-methyl-2-chloropyridinium chloride is added to this solution, which is then stirred for 15 min. 1 equivalent of guanidinium chloride and 2.6 ml of diisopropylethylamine are then added, and the mixture is stirred at room temperature for 1 h. After the customary working up, and following chromatography on silica gel (flash method, ethyl acetate/10% methanol) and subsequent treatment with HCl, N-diaminomethylene-2-methyl-4-cyano-5-methylsulphonylbenzamide, hydrochloride, is obtained, m.p. 227°–228°.

The following are obtained in an analogous manner by reacting guanidinium chloride with 2-ethyl-4-cyano-5-methylsulphonylbenzoic acid: N-diaminomethylene-2-ethyl-4-cyano-5-methylsulphonylbenzamide, hydrochloride;

with 2,4-dicyano-5-methylsulphonylbenzoic acid: N-diaminomethylene-2,4-dicyano-5-methylsulphonylbenzamide;

with 2-methoxy-4-cyano-5-methylsulphonylbenzoic acid: N-diaminomethylene-2-methoxy-4-cyano-5-methylsulphonylbenzamide;

with 2-fluoromethyl-4-cyano-5-methylsulphonylbenzoic acid: N-diaminomethylene-2-fluoromethyl-4-cyano-5-methylsulphonylbenzamide;

with 2-difluoromethyl-4-cyano-5-methylsulphonylbenzoic acid: N-diaminomethylene-2-difluoromethyl-4-cyano-5-methylsulphonylbenzamide;

with 2-ethynyl-4-cyano-5-methylsulphonylbenzoic acid: N-diaminomethylene-2-ethynyl-4-cyano-5-methylsulphonylbenzamide;

with 2-pentafluoroethyl-4-cyano-5-methylsulphonylbenzoic acid: N-diaminomethylene-2-pentafluoroethyl-4-cyano-5-methylsulphonylbenzamide.

EXAMPLE 13

A solution of 1.8 g of methyl 2-methyl-4-bromo-5-methylsulphonylbenzoate [obtainable in accordance with Ex. 1] and 1.5 g of guanidine in 50 ml of methanol is boiled for five hours, and the solvent is subsequently removed. The residue is treated with water and the remaining crystalline crop is filtered off with suction and treated with dil. sodium hydroxide solution. The solid residue is filtered off and recrystallized from ethanol, and N-diaminomethylene-2-methyl-4-bromo-5-methylsulphonylbenzamide is obtained, m.p. 207°–208°.

The following are obtained in an analogous manner by reacting guanidine with methyl 2-methyl-4-chloro-5-methylsulphonylbenzoate: N-diaminomethylene-2-methyl-4-chloro-5-methylsulphonylbenzamide, m.p. 204°–205°;

with methyl 2-amino-4-chloro-5-methylsulphonylbenzoate: N-diaminomethylene-2-amino-4-chloro-5-methylsulphonylbenzamide, m.p. 245°;

with methyl 2,4-dichloro-5-methylsulphonylbenzoate: N-diaminomethylene-2,4-dichloro-5-methylsulphonylbenzamide, m.p. 189°–190°;

with methyl 2-ethyl-4-chloro-5-methylsulphonylbenzoate: N-diaminomethylene-2-ethyl-4-chloro-5-methylsulphonylbenzamide, m.p. 160°–162°;

with methyl 2-methyl-4-bromo-5-aminosulphonylbenzoate: N-diaminomethylene-2-methyl-4-bromo-5-aminosulphonylbenzamide, m.p. 204°;

with methyl 2-methyl-4-bromo-5-N,N-dimethylaminosulphonylbenzoate: N-diaminomethylene-2-methyl-4-bromo-5-N',N'-dimethylaminosulphonylbenzamide, m.p. 222°–223°;

with methyl 2-chloro-4-fluoro-5-methylsulphonylbenzoate: N-diaminomethylene-2-chloro-4-fluoro-5-methylsulphonylbenzamide;

with methyl 2-methyl-4-chloro-5-phenylsulphonylbenzoate: N-diaminomethylene-2-methyl-4-chloro-5-phenylsulphonylbenzamide, m.p. 185°–187°; m.p. 230°–232° (hydrochloride);

with methyl 2-fluoromethyl-4-chloro-5-methylsulphonyl benzoate: N-diaminomethylene-2-fluoromethyl-4-chloro-5-methylsulphonylbenzamide;

with methyl 2-ethyl-4-bromo-5-methylsulphonylbenzoate: N-diaminomethylene-2-ethyl-4-bromo-5-methylsulphonylbenzamide, m.p. 169°–171°;

with methyl 2-methyl-4-fluoro-5-methylsulphonylbenzoate: N-diaminomethylene-2-methyl-4-fluoro-5-methylsulphonylbenzamide, m.p. 208°–210°;

with methyl 2-ethyl-4-fluoro-5-methylsulphonylbenzoate: N-diaminomethylene-2-ethyl-4-fluoro-5-methylsulphonylbenzamide;

with methyl 2,4-difluoromethyl-5-methylsulphonylbenzoate: N-diaminomethylene-2,4-difluoromethyl-5-methylsulphonylbenzamide, m.p. 260°;rs with methyl 2-ethynyl-4-bromo-5-methylsulphonylbenzoate: N-diaminomethylene-2-ethynyl-4-bromo-5-methylsulphonylbenzamide;

with methyl 2-nitro-4-fluoro-5-methylsulphonylbenzoate: N-diaminomethylene-2-nitro-4-fluoro-5-methylsulphonylbenzamide;

with methyl 2-methoxy-4-formyl-5-methylsulphonylbenzoate: N-diaminomethylene-2-methoxy-4-formyl-5-methylsulphonylbenzamide;

with methyl 2-difluoromethyl-4-formyl-5-methylsulphonylbenzoate: N-diaminomethylene-2-difluoromethyl-4-formyl-5-methylsulphonylbenzamide;

with methyl 2-ethynyl-4-chloro-5-methylsulphonylbenzoate: N-diaminomethylene-2-ethynyl-4-chloro-5-methylsulphonylbenzamide;

with methyl 2-pentafluoroethyl-4-fluoro-5-methylsulphonylbenzoate: N-diaminomethylene-2-pentafluoroethyl-4-fluoro-5-methylsulfonylbenzamide;

with methyl 2-cyano-4-formyl-5-methylsulphonylbenzoate: N-diaminomethylene-2-cyano-4-formyl-5-methylsulphonylbenzamide;

The examples given below relate to pharmaceutical preparations.

EXAMPLE A

Injection Vials

A solution of 100 g of an active compound of the formula I and 5 g of disodium hydrogen phosphate in 3 l of double-distilled water is adjusted to pH 6.5 using 2N hydrochloric acid, sterilized by filtration and used to fill injection vials; the solution in the vials is then lyophilized under sterile conditions and the vials are then sealed in a sterile manner. Each injection vial contains 5 mg of active compound.

EXAMPLE B

Suppositories

A mixture of 20 g of an active compound of the formula I is melted together with 100 g of soyabean lecithin and 1400 g of cocoa butter and the mixture is poured into molds and allowed to cool. Each suppository contains 20 mg of active compound.

EXAMPLE C

Solution

A solution is prepared consisting of 1 g of an active compound of the formula I, 9.38 g of $NaH_2PO_4 \cdot 2\ H_2O$, 28.48 g of $Na_2HPO_4 \cdot 12\ H_2O$ and 0.1 g of benzalkonium chloride in 940 ml of double-distilled water. The solution is adjusted to pH 6.8, made up to 1 l and sterilized by irradiation. This solution can be used in the form of eye drops, for example.

EXAMPLE D

Ointment 500 mg of an active compound of the formula I are mixed with 99.5 g of vaseline under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed, in a customary manner, into tablets such that each tablet contains 10 mg of active compound.

EXAMPLE F

Coated Tablets

Tablets are compressed in analogy with Example E, which tablets are subsequently coated, in a customary manner, with a coating consisting of sucrose, potato starch, talc, gum tragacanth and coloring matter.

EXAMPLE G

Capsules

Hard gelatin capsules are filled, in a customary manner, with 2 kg of active compound of the formula I such that each capsule contains 20 mg of the active compound.

EXAMPLE H

Ampoules

A solution of 1 kg of active compound of the formula I in 60 l of double-distilled water is sterilized by filtration and used to fill ampoules; the solution in the ampoules is lyophilized under sterile conditions and the ampoules are sealed in a sterile manner. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. An ortho-substituted benzoic acid compound of the formula I

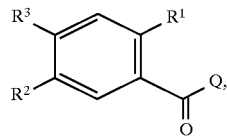

in which $R^1$ is A, $CF_3$, $CH_2F$, $CHF_2$, $C_2F_5$, CN, $NO_2$, C≡CH, —O—$R^4$ or —S—$R^4$, $R^2$ is $CF_3$, —$SO_n$—$R^6$ or —$SO_2NR^4R^5$, $R^3$ is A, CN, Hal, COA, CHO, $CSNR^7R^8$ or $CONR^7R^8$, Q is —N=C($NH_2$)$_2$, $R^4$ is H, A, cycloalkyl having from 5 to 7 C atoms, cycloalkylmethyl having from 6 to 8 C atoms, $CF_3$, $CH_2F$, $CHF_2$, $CH_2CF_3$, Ph or —$CH_2$—Ph, $R^5$ is H or A, or else $R^4$ and $R^5$ are together alkylene having from 4 to 5 C atoms, where one $CH_2$ group can also be replaced by O, S, CO, NH, N—A or N—$CH_2$—Ph, $R^6$ is A or Ph, $R^7$ and $R^8$ are in each case, independently of one another, H, A or Ac, A is alkyl having from 1 to 6 C atoms, X is O, S or $NR^5$, Ph is phenyl which is unsubstituted or is substituted once, twice or three times by A, OA, $NR^4R^5$, F, Cl, Br, I or $CF_3$, Ac is alkanoyl having from 1 to 10 C atoms, or aroyl having from 7 to 11 C atoms, and n is 1 or 2, or the pharmaceutically tolerated salt thereof.

2. A compound:
   (a) N-Diaminomethylene-2-methyl-4-bromo-5-methylsulphonylbenzamide;
   (b) N-diaminomethylene-2-methyl-4-chloro-5-methylsulphonylbenzamide;
   (c) N-diaminomethylene-2-methyl-4-cyano-5-methylsulphonylbenzamide;
   (d) N-diaminomethylene-2-ethyl-4-bromo-5-methylsulphonylbenzamide;
   (e) N-diaminomethylene-2-ethyl-4-chloro-5-methylsulphonylbenzamide;
   (f) A N-diaminomethylene-2-methyl-4-fluoro-5-methylsulphonylbenzamide;
   (g) N-diaminomethylene-2-ethyl-4-fluoro-5-methylsulphonylbenzamide;

according to claim 1, and also the physiologically tolerable salts thereof.

3. A process for producing a pharmaceutical composition which comprises bringing a compound of the formula I according to claim 1, and/or one of its physiologically tolerable salts, together with at least one solid, liquid or semi-liquid carrier substance or auxiliary substance, into a suitable form for administration.

4. A pharmaceutical composition, comprising at least one compound of the formula I, according to and/or of one of its physiologically harmless salts, and a physiologically suitable auxiliary.

5. A method for the treatment or prevention of arrhythmias, angina pectoris or infarctions which comprises administering to a patient in need thereof a compound of the formula I according to claim 1 or physiologically tolerable salts thereof.

6. A compound of claim 1, wherein $R^1$ is A and $R^2$ is —$SO_2$—$CH_3$.

7. A compound of claim 1, wherein $R^1$ is A, OH, or OA, and $R^2$ is $SO_2CH_3$.

8. A compound of claim 1, wherein $R^1$ is A, and $R^3$ is CN, CHO, Cl or Br.

9. A compound of claim 1, wherein $R^2$ is $SO_2$—$CH_3$, and $R^3$ is A, F, Cl, Br or CN.

10. A compound of claim 1, wherein $R^1$ is A, $R^2$ is —$SO_2$—$CH_3$ and $R^3$ is A, F, Cl, Br or CN.

11. A compound of claim 1, wherein $R^1$ is $CH_3$ or $C_2H_5$, $R^3$ is F, Cl, Br, CHO or COA, and $R^2$ is —$SO_2$—$CH_3$.

12. A method for treating or controlling a disease treatable by inhibition of the cellular $Na^+/H^+$ antiporter which comprises administering a cellular $Na^+/H^+$ antiporter inhibiting effective amount of an ortho-substituted benzoic acid compound of claim 1 to a human or animal in need thereof.

13. The method of claim 12, wherein the ortho-substituted benzoic acid compound is administered in a daily dose of 0.0001–0.1 mg/kg of body weight.

14. The method of claim 5, wherein the compound of formula I is administered in a daily dose of 0.0001–0.1 mg/kg of body weight.

15. A compound of claim 1, wherein $R^1$ is A or CN and $R^3$ is Hal, A or CN.

* * * * *